United States Patent
Eckerline et al.

(10) Patent No.: US 10,149,665 B2
(45) Date of Patent: Dec. 11, 2018

(54) ACCESSORY DEVICE FOR EUS-FNA NEEDLE FOR GUIDEWIRE PASSAGE

(71) Applicant: BOSTON SCIENTIFIC SCIMED, INC., Maple Grove, MN (US)

(72) Inventors: Katharine Eckerline, Boston, MA (US); Sean P. Fleury, Brighton, MA (US); Louis Del Ponte, Hopkinton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 359 days.

(21) Appl. No.: 14/937,291

(22) Filed: Nov. 10, 2015

(65) Prior Publication Data
US 2016/0157839 A1 Jun. 9, 2016

Related U.S. Application Data

(60) Provisional application No. 62/086,973, filed on Dec. 3, 2014.

(51) Int. Cl.
*A61B 5/00* (2006.01)
*A61B 10/02* (2006.01)
(Continued)

(52) U.S. Cl.
CPC ........... *A61B 10/0283* (2013.01); *A61B 8/12* (2013.01); *A61B 17/3478* (2013.01);
(Continued)

(58) Field of Classification Search
CPC .............. A61B 5/6851; A61B 5/6852; A61B 10/0283; A61B 17/1697; A61B 17/3478; A61B 17/3496
See application file for complete search history.

(56) References Cited

U.S. PATENT DOCUMENTS 3,630,192 A * 12/1971 Jamshidi ............ A61B 10/025
219/229
4,487,209 A * 12/1984 Mehl .................... A61B 10/025
600/567
(Continued)

FOREIGN PATENT DOCUMENTS

WO 2014/077025 5/2014
WO 2014/165783 10/2014

OTHER PUBLICATIONS

Keehan et al., "*Catheter and Specialty Needle Alloys*", Material and Processes for Medical Devices Conferences & Exposisition, Minneapolis, Aug. 10-12, 2009, 6pgs.
Sarkaria et al., "*Endoscoopic Ultrasonographic Access and Drainage of the Common Bile Duct*", Gastrointest Endoscopy Clin N. Am. No. 23; 2013, pp. 435-451.

*Primary Examiner* — Max Hindenburg
(74) *Attorney, Agent, or Firm* — Fay Kaplun & Marcin, LLP

(57) ABSTRACT

A combined system for diagnostic and therapeutic procedures includes a needle extending longitudinally from a proximal end to a distal end and including a lumen extending therethrough, the distal end including a sharp grind for cutting a tissue sample to be collected in the lumen of the needle and a protective sheath sized and shaped to be inserted through the lumen of the needle such that a distal end of the protective sheath extends distally past the distal end of the needle, the protective sheath extending longitudinally from a proximal end to the distal end and including a lumen extending therethrough.

12 Claims, 2 Drawing Sheets

(51) Int. Cl.
*A61B 8/12* (2006.01)
*A61M 25/09* (2006.01)
*A61M 29/02* (2006.01)
*A61B 17/34* (2006.01)
*A61B 10/04* (2006.01)
*A61B 17/22* (2006.01)

(52) U.S. Cl.
CPC ......... *A61B 17/3496* (2013.01); *A61M 25/09* (2013.01); *A61M 29/02* (2013.01); *A61B 2010/045* (2013.01); *A61B 2017/22038* (2013.01)

(56) References Cited

U.S. PATENT DOCUMENTS

| | | | | |
|---|---|---|---|---|
| 8,043,229 B2 * | 10/2011 | Mulvihill | ............. | A61B 10/025 |
| | | | | 600/562 |
| 8,048,030 B2 * | 11/2011 | McGuckin, Jr. | ... | A61B 17/3417 |
| | | | | 604/164.01 |
| 8,517,955 B2 * | 8/2013 | Keast | ................. | A61B 10/0266 |
| | | | | 600/564 |
| 9,216,269 B2 * | 12/2015 | Choi | .................. | A61B 17/3415 |
| 9,289,231 B2 * | 3/2016 | Clancy | .................. | A61B 17/34 |
| 2005/0245876 A1 | 11/2005 | Khosravi et al. | | |
| 2006/0009737 A1 | 1/2006 | Whiting et al. | | |
| 2010/0048900 A1 | 2/2010 | Bakos | | |

\* cited by examiner

ACCESSORY DEVICE FOR EUS-FNA NEEDLE FOR GUIDEWIRE PASSAGE

PRIORITY CLAIM

This application claims priority to U.S. Provisional Patent Application Ser. No. 62/086,973 filed Dec. 3, 2014; the disclosure of which is incorporated herewith by reference.

BACKGROUND

As therapeutic Endoscopic Ultrasound (EUS) procedures continue to advance, it is important for a guidewire to safely pass through an EUS-FNA needle. Therapeutic EUS applications requiring guidewire passage include, for example, EUS-guided biliary, pseudocyst and gallbladder drainage. In some cases, particularly when the EUS-FNA needle and guidewire are passed through a tortuous path, the guidewire inserted through a standard EUS-FNA needle may be sheared by the sharp grind of the needle during manipulation, compromising the ability to manipulate the wire and/or exchange devices. This may result in a loss of access to the target area and an increase in procedure time and cost. In addition, parts of the wire and coating may be left behind in the anatomyrequiring additional intervention and potential trauma to the patient.

SUMMARY

The present disclosure is directed to a combined system for diagnostic and therapeutic procedures, comprising a needle extending longitudinally from a proximal end to a distal end and including a lumen extending therethrough, the distal end including a sharp grind for cutting a tissue sample to be collected in the lumen of the needle and a protective sheath sized and shaped to be inserted through the lumen of the needle such that a distal end of the protective sheath extends distally past the distal end of the needle, the protective sheath extending longitudinally In an embodiment, the system may further comprise a guidewire extending from a proximal end to a distal end and sized and shaped to be inserted through the lumen of the protective sheath.

In an embodiment, the needle may include an engaging element at the proximal end thereof.

In an embodiment, the protective sheath may include a corresponding engaging structure at the proximal end thereof engagable with the engaging element of the needle so that, when the protective sheath is inserted in the lumen of the needle, the engaging element and the corresponding engaging structure engage one another to lock the protective sheath relative to the needle.

In an embodiment, the engaging element may be a luer fitting.

In an embodiment, the system further comprises a stylet extending from a proximal end to a distal end and sized and shaped to be inserted through the lumen of the needle.

In an embodiment, the protective sheath may be formed of one of Nitinol and Cobalt Chromium.

In an embodiment, an outer diameter of the protective sheath may range from between 0.030 inches (0.762 mm) and 0.035 inches (0.889 mm).

In an embodiment, an inner diameter of the protective sheath may range from between 0.0265 inches (0.673 mm) and 0.030 inches (0.762 mm).

In an embodiment, the distal end of the protective sheath may be beveled.

In an embodiment, the protective sheath may include a metal ring along a distal portion thereof which, when the protective sheath is inserted in the lumen of the needle, is positioned within the distal end of the needle.

The present disclosure is also directed to a device for treating tissue, comprising a protective sheath extending longitudinally from a proximal end to a distal end and including a lumen extending therethrough, the protective sheath sized and shaped to be inserted through a lumen of a needle such that when the distal end of the protective sheath extends distally beyond a distal end of the needle, a guidewire inserted through the lumen of the protective sheath is protected from a sharp tip of the needle.

In an embodiment, the protective sheath may be formed of one of Nitinol and Cobalt Chrommium.

In an embodiment, the protective sheath includes a metal ring along a distal portion thereof which, when the protective sheath is inserted in the lumen of the needle, is positioned within the distal end of the needle.

In an embodiment, an outer diameter of the protective sheath may range from between 0.030 inches (0.762 mm) and 0.035 inches (0.889 mm) and an inner diameter of the protective sheath may range from between 0.0265 inches (0.673 mm) and 0.030 inches (0.762 mm).

The present disclosure is also directed to a method for treating tissue, comprising inserting a needle to a target site within a patient body with a stylet received within a lumen thereof, a distal end of the stylet extending distally past a distal end of the needle to prevent tissue from being collected within the lumen of the needle during insertion, removing the stylet from the needle and inserting a protective sheath through the lumen of the needle such that a distal end of the protective sheath extends distally past the distal end of the needle, and inserting a guidewire through the lumen of the protective sheath until a distal end of the guidewire is within the target site.

BRIEF DESCRIPTION

DETAILED DESCRIPTION

Figure 1:
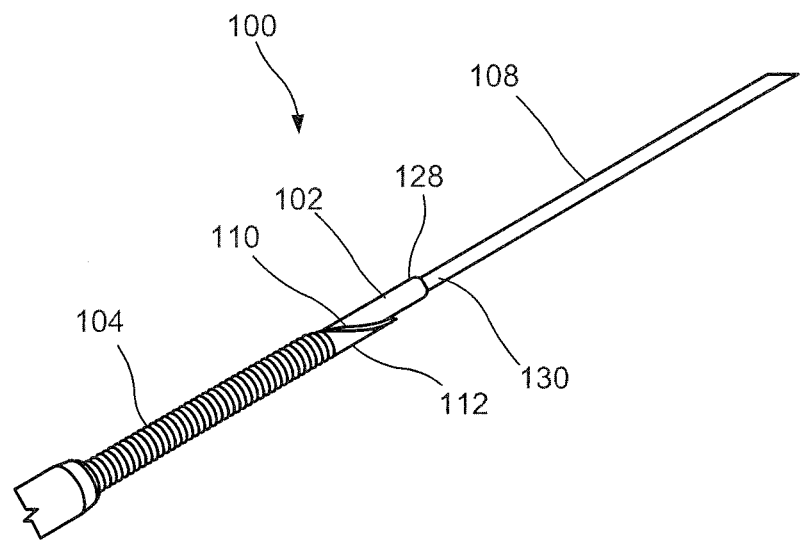
FIG. 1 shows a perspective view of a distal portion of a system according to an exemplary embodiment of the present disclosure.
Figure 2:
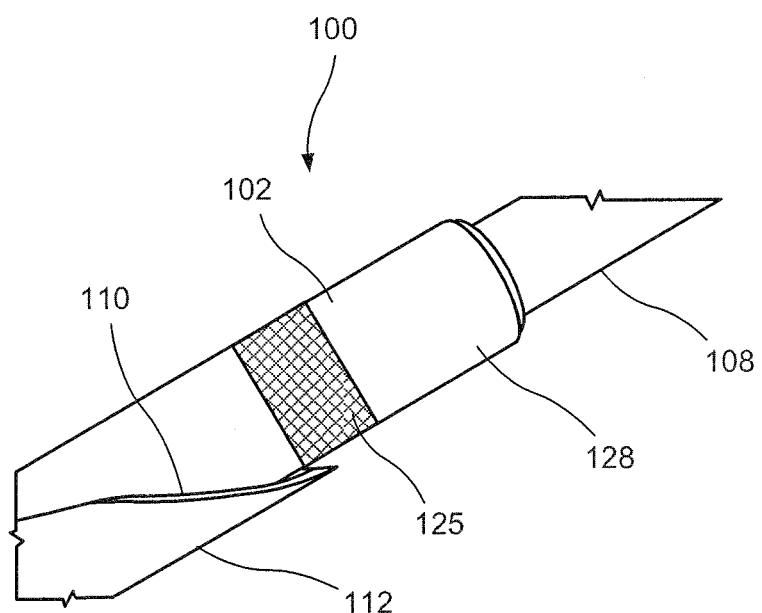
FIG. 2 shows an enlarged perspective view of the distal portion of the system of FIG. 1.

The present disclosure may be further understood with reference to the following description and the appended drawings, wherein like elements are referred to with the same reference numerals. The present disclosure is directed to endoscopic devices and, in particular, devices for use with EUS-FNA needles. Exemplary embodiments of the present disclosure describe a system comprising a protective sheath insertable through a lumen of an EUS-FNA needle to act as a barrier between a sharp tip of the needle and a guidewire passed therethrough so that the needle may be converted to a therapeutic device providing access to a target site. It should be noted that the terms "proximal" and "distal," as used herein are intended to refer to a direction toward (proximal) and away from (distal) a user of the device, As shown in FIGS. 1-4, a system 100 comprises a protective sheath 102 insertable through a lumen 106 of a needle 104 to protect a guidewire 108 passed therethrough from being sheared by a sharp tip 110 at a distal end 112 of the needle 104, which may be formed as, for example, a sharp grind. In particular, the needle 104 may be an EUS-FNA needle visible under ultrasound guidance and including the sharp tip 110 to facilitate the penetration of target tissue (e.g., for tissue sample acquisition) within a patient's body. It may also be desirable to insert a guidewire 108 through the needle 104, for example, during EUS-guided drainage procedures such as EUS-guided biliary, pseudocyst and gall bladder drainage. Facilitating the use of the EUS-FNA needle for both tissue sample acquisition and guide-wire assisted procedures such as drainage renders the device more versatile and may simplify and shorten procedures. For example, a guidewire may be required to provide passage of other devices such as cystatomes, balloons and/or stents during a drainage procedure. Insertion of a guidewire through a blunt catheter or hypotube rather than an EUS-FNA needle including a sharp grind to prevent shearing would require the use of a separate needle device for tissue acquisition. FNA needles are much more frequently used and the ability to convert an FNA needle into a blunt access needle using the protective sheath 102 is advantageous and efficient. Use of the protective sheath 102 with the needle 104 improves patient safety in drainage applications. The system 100 may further comprise a stylet 124 configured to be received within the lumen 106 of the needle 104 during an initial insertion of the needle 104 to a target site within a patient body. In use, the needle 104 and stylet 124 may be inserted to the target site with a distal end 126 of the stylet 124 extending distally of the distal end 112 of the needle 104 to prevent non-targeted tissue from entering the lumen 106 during insertion of the needle 104 to the target site. When it is desired to insert a guide wire to a target site adjacent to a distal end of the needle 104, the stylet 124 may be removed and the protective sheath 102 may then be inserted through the lumen 106 so that a distal end 128 of the protective sheath 102 extends distally of the distal end 112 of the needle 104. The guidewire 108 may then be passed through a lumen 130 of the protective sheath 102 to the target site so that other devices necessary for the drainage of the target site may be guided therealong as would be understood by those skilled in the art.

Figure 3:
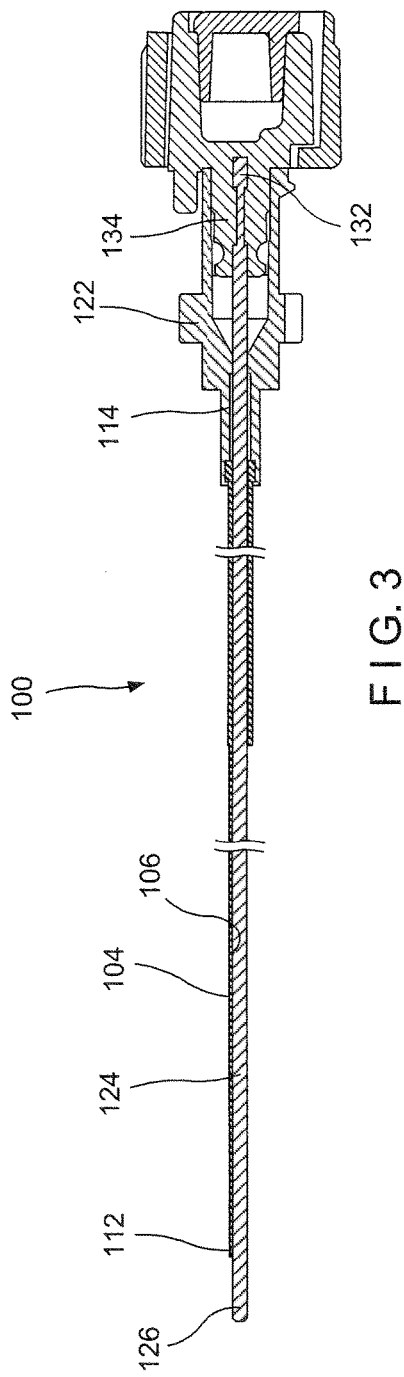
FIG. 3 shows a longitudinal cross-sectional view of a needle and stylet of the system of FIG. 1.
Figure 4:
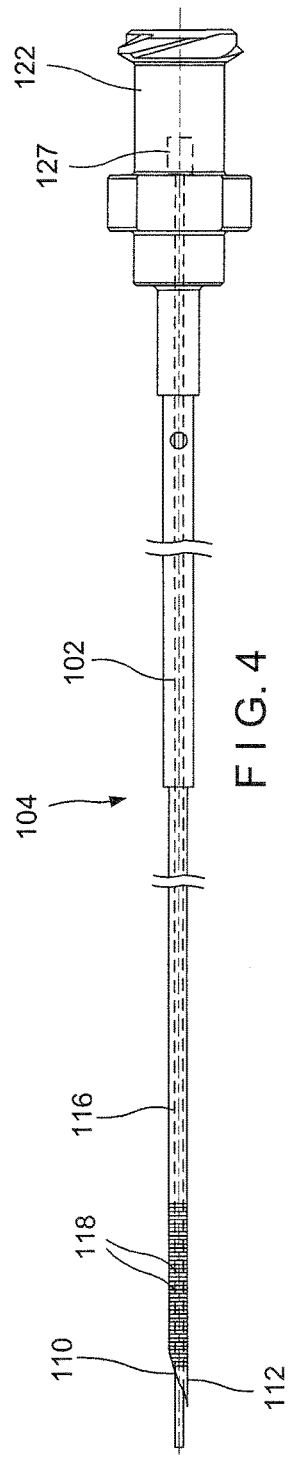
FIG. 4 shows a longitudinal side view of the needle of the system of FIG. 1.

As shown in FIGS. 3-4, the needle 104 may be a standard EUS-FNA needle extending longitudinally from a proximal end 114 to the distal end 112 and defining the lumen 106 extending therethrough. An outer surface 116 of the needle 104 may include echogenic enhancing features 118 such as, for example, one or more grooves extending along and/or about a distal portion 120 of the needle 104. The needle 104 may include an engaging element 122 such as, for example, a luer fixture, at the proximal end 114 to engage a corresponding fixture or structure at a proximal end of the stylet 124 and/or protective sheath 102, as will be described in further detail below.

The stylet 124 may also extend longitudinally from a proximal end 132 to the distal end 126 and include a corresponding engaging element 134 at the proximal end 132 for engaging the engaging element 122 of the needle 104. A length of the stylet 124 may be selected so that, when the stylet 124 is inserted through the lumen 106 of the needle 104 and the corresponding engaging element 134 engages the engaging element 122 of the needle 104, the distal end 126 of the stylet 124 extends slightly distal of the distal end 112 of the needle 104.

The protective sheath 102 extends from a proximal end (not shown) to the distal end 128 and defines a lumen 130 extending therethrough. The distal end 128 may be beveled, rounded or otherwise shaped to prevent damage to surrounding tissue as would be understood by those skilled in the art. The protective sheath 102 is sized and shaped for insertion through the lumen 106 of the needle 104 and the lumen 130 of the protective sheath 102 is sized and shaped to slidably receive the guidewire 108 therein. The protective sheath 102 is formed of a material that is sufficiently flexible to be inserted through the needle 104 even when the needle 104 extends along a tortuous path (e.g. along a natural body lumen in the patient's body) while also having sufficient hardness and column strength to prevent enable it to be pushed through the needle 104 and to prevent shearing despite contact with the sharp tip 110. Furthermore, the material must be able to present these qualities in a thin-walled design. For example, the protective sheath 102 may be formed of Nitinol, Cobalt Chromium or any other materials having the properties described above. In one example, the protective sheath 102 may have an outer diameter configured to be passed through a 19 gauge needle, which may have an inner diameter of approximately 0.037 inches (0.940 mm) and have an inner diameter sized to receive a 0.025 inch (0.635 mm) diameter guidewire. The protective sheath 102 may, for example, be formed of Nitinol and have a wall thickness of 0.005 inches (0.127 mm). In an exemplary embodiment, the protective sheath 102 may have an outer diameter ranging from between 0.030 inches (0.762 mm) and 0.035 inches (0.889 mm) and an inner diameter ranging from between 0.0265 inches (0.673 mm) to 0.030 inches (0.762 mm). In another embodiment, the protective sheath 102 may be reinforced along a portion of its length (e.g., a portion adjacent to a distal end thereof) which is likely to come into contact with the sharp tip 110. For example, a distal portion of the sheath 102 may include a metal ring 125 stiffer than the remainder of the sheath 102 so that this portion would have increased resistance to damage from contact with the sharp tip 110 when the protective sheath 102 is extended distally out of the needle 104.

The protective sheath 102 may also include a handle having an engaging structure 127 at the proximal end thereof which, when the protective sheath 102 is inserted through the lumen 106 of the needle 104, engages the engaging element 122 of the needle 102 to lock a position of the protective sheath 102 relative to the needle 104. The engaging structure 122 may be substantially similar to the corresponding engaging element 134 of the stylet 124. The engaging structure may be, for example, a luer fixture. A length of the protective sheath 102 may be selected so that, when the protective sheath 102 is inserted into the lumen 106 and the engaging structure 2 engages the engaging element 122 of the needle 104, the distal end 128 extends distally of the sharp tip 110 of the needle 104 to protect the guidewire 108 from shearing as it is inserted through the lumen of the protective sheath 102.

In use, the needle 104 is advanced through, for example, through an echo-endoscope and inserted to a target site within an extraluminal, adjacent structure identified under ultrasound with the stylet 124 inserted through the lumen 106 thereof. As indicated above, the needle 104 and the stylet 124 are configured to be inserted through even tortuous paths of the body to the target site. The engaging element 122 of the needle 104 and the corresponding engaging element 134 of the stylet 124 are engaged with one another such that the distal end 126 of the stylet 124 extends just distally of the distal end 112 of the needle 104 to prevent damage to the scope in tortuous anatomy. The stylet 124 is drawn proximally relative to the needle 104 to expose the sharp tip 110 so that the sharp tip 110 may puncture the target site, providing access thereto. Subsequent to puncture, the stylet 124 may be advanced distally relative to the needle 104 to expel any undesired tissue from being collected within the lumen 106 of the needle 104. Once the target site has been reached, the corresponding engaging element 134 is disengaged from the engaging element 122 of the needle 104 and the stylet 124 is removed therefrom. The protective sheath 102 is then inserted through the lumen 106 of the needle 104 until the distal end 128 of the protective sheath 102 extends distally past the distal end 112 of the needle 104. The engaging feature of the protective sheath 102 may be engaged with the engaging element 122 of the needle 104 to lock the protective sheath 102 in a desired position relative to the needle 104.

The guidewire 108 is then inserted through the lumen 130 of the protective sheath 102 to the target site. The guidewire 108 is advanced through the protective sheath 102 during a device exchange in which the needle 104 and protective sheath 102 is removed to ensure that the guidewire 108 does not lose access to the target site as the needle 104 is withdrawn from the body so that other devices necessary for the EUS application (e.g., cystatomes, balloons, stents) may be guided over the guide wire 108 to the target site. A distal end of the guidewire 108 may be anchored in position in the target site so that other EUS devices may be guided therealong to, for example, dilate the target site to facilitate drainage thereof. Multiple devices may be exchanged over the guidewire 108, as necessary, to treat the target site. Once the target site has been treated, as desired, the devices and the guidewire 108 may be removed from the target site. In cases in which a tissue acquisition is desired, removing the protective sheath 102 from the lumen 106 of the needle 104 and reinserting the stylet 124 thereinto returns the needle 104 to its initial functionality as an FNA needle for tissue acquisition.

It will be apparent to those skilled in the art that variations can be made in the structure and methodology of the present disclosure, without departing from the scope of the disclosure. Thus, it is intended that the present disclosure cover the modifications and variations of this disclosure provided that they come within the scope of the appended claims and their equivalents.

What is claimed is:

1. A combined system for diagnostic and therapeutic procedures, comprising:
   a needle extending longitudinally from a proximal end to a distal end and including a lumen extending therethrough, the distal end including a sharp grind for cutting a tissue sample to be collected in the lumen of the needle; and
   a protective sheath sized and shaped to be inserted through the lumen of the needle such that a distal end of the protective sheath extends distally past the distal end of the needle, the protective sheath extending longitudinally from a proximal end to the distal end and including a lumen extending therethrough, wherein the distal end of the protective sheath is rounded to prevent damage to tissue, wherein the protective sheath includes a metal ring along a distal portion thereof which, when the protective sheath is inserted in the lumen of the needle, is positioned within the distal end of the needle.

2. The system of claim 1, further comprising a guidewire extending from a proximal end to a distal end and sized and shaped to be inserted through the lumen of the protective sheath.

3. The system of claim 1, wherein the needle includes an engaging element at the proximal end thereof.

4. The system of claim 3, wherein the protective sheath includes a corresponding engaging structure at the proximal end thereof engagable with the engaging element of the needle so that, when the protective sheath is inserted in the lumen of the needle, the engaging element and the corresponding engaging structure engage one another to lock the protective sheath relative to the needle.

5. The system of claim 3, wherein the engaging element is a luer fitting.

6. The system of claim 1, further comprising a stylet extending from a proximal end to a distal end and sized and shaped to be inserted through the lumen of the needle.

7. The system of claim 1, wherein the protective sheath is formed of one of Nitinol and Cobalt Chromium.

8. The system of claim 1, wherein an outer diameter of the protective sheath ranges from between 0.030 inches and 0.035 inches.

9. The system of claim 1, wherein an inner diameter of the protective sheath ranges from between 0.0265 inches and 0.030 inches.

10. A device for treating tissue, comprising a protective sheath extending longitudinally from a proximal end to a distal end and including a lumen extending therethrough, the protective sheath sized and shaped to be inserted through a lumen of a needle such that when the distal end of the protective sheath extends distally beyond a distal end of the needle, a guidewire inserted through the lumen of the protective sheath is protected from a sharp tip of the needle, wherein the distal end of the protective sheath is rounded to prevent damage to tissue, wherein the protective sheath includes a metal ring along a distal portion thereof which, when the protective sheath is inserted in the lumen of the needle, is positioned within the distal end of the needle.

11. The device of claim 10, wherein the protective sheath is formed of one of Nitinol and Cobalt Chromium.

12. The device of claim 10, wherein an outer diameter of the protective sheath ranges from between 0.030 inches and 0.035 inches and an inner diameter of the protective sheath ranges from between 0.0265 inches and 0.030 inches.

* * * * *